US005247104A

United States Patent [19]

DeLuca et al.

[11] Patent Number: 5,247,104

[45] Date of Patent: Sep. 21, 1993

[54] PREPARATION OF 1α, 24-DIHYDROXYVITAMIN D ANALOGS

[75] Inventors: Hector F. DeLuca, Deerfield; Heinrich K. Schnoes, Madison, both of Wis.

[73] Assignee: Wisconsin Alumni Research Foundation, Madison, Wis.

[21] Appl. No.: 971,405

[22] Filed: Nov. 4, 1992

[51] Int. Cl.[5] .......... C07J 9/00

[52] U.S. Cl. .......... 552/653

[58] Field of Search .......... 552/653

[56] References Cited

U.S. PATENT DOCUMENTS 4,588,528 5/1986 DeLuca et al. .

4,847,012 7/1989 DeLuca et al. .

4,866,048 9/1989 Calverley et al. .

OTHER PUBLICATIONS

Hiroshi Sai et al, Synthesis and Biological Activity of (22,24R)-and (22E,24S)-1α,24-Dihydroxy-22-dehydrovitamin D3, Chem. Pharm. Bull. vol. 32, pp. 3866-3872 (1984).

*Primary Examiner*—Alan Siegel

*Attorney, Agent, or Firm*—Andrus, Sceales, Starke & Sawall

[57] ABSTRACT

A synthesis of 1α,24(R)- and 1α,24(S)-dihydroxy-22(E)-dehydrovitamin $D_3$ compounds. This process involves two major operations, namely, (a) the attachment of the required side chain to an existing vitamin D-22-aldehyde derivative to obtain an enone derivative as an intermediate, and (b) the stereoselective reduction of the ketone group of said enone intermediate to obtain the desired 24(R)- and 24(S)-hydroxyvitamin D compounds. The vitamin D enone derivatives generated as intermediates in the process are also new compounds.

1 Claim, No Drawings

PREPARATION OF 1α, 24-DIHYDROXYVITAMIN D ANALOGS

BACKGROUND OF THE INVENTION

This invention relates to vitamin D compounds. More specifically the invention relates to a new synthesis of 1α,24(R)-and 1α,24(S)-dihydroxy-22(E)-dehydrovitamin $D_3$, and to novel vitamin D derivatives generated as intermediates in the synthetic process.

The 24(R)- and 24(S)-epimers of 1α,24-dihydroxy-22-dehydrovitamin $D_3$ are known compounds, their preparation being disclosed in U.S. Pat. No. 4,588,528. This known preparation is, however, a lengthy multi-step process, which entails, moreover, a difficult separation of stereoisomers at an early stage of the synthesis. Since the compounds possess, however, high biological activity, which renders them useful as potential therapeutic agents for the treatment of calcium metabolism-related disorders, such as renal osteodystrophy, hyperparathyroidism, osteoporosis, or of skin disorders such as psoriasis, the development of a new synthetic process, which would provide for the more efficient and convenient preparation of these compounds becomes an important objective.

GENERAL DESCRIPTION OF PROCESS

This objective has been realized by a new process disclosed herein, which provides both the above-named 24(R)-and 24(S)-1α,24-dihydroxy-22(E)-dehydrovitamin $D_3$ compounds. This process essentially involves two major operations, namely: (a) the attachment of the required side chain to an existing vitamin D-22-aldehyde derivative to obtain an enone derivative as an intermediate, and (b) the stereoselective reduction of the ketone group of said enone intermediate to obtain the desired 24(R)- and 24(S)-hydroxyvitamin D compounds.

Suitable starting materials for the new process are vitamin D-22-aldehydes of the general structure,

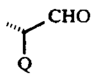

where Q represents a 1α-hydroxylated vitamin D nucleus having the structure below,

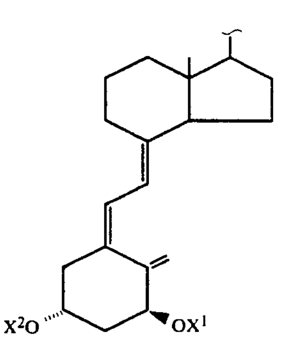

wherein $X^1$ and $X^2$, which may be the same or different represent a hydroxy-protecting group, as further defined below. Such 1α-hydroxyvitamin D-22-aldehydes are known compounds (DeLuca et al., U.S. Pat. No. 4,847,012; Calverley et al. U.S. Pat. No. 4,866,048). Side chain attachment is accomplished in a one-step procedure, namely by the condensation of the vitamin D-22-aldehyde with isobutyrylmethylene triphenylphosphorane using conditions appropriate for ylid-type coupling reactions. There is obtained an α,β-unsaturated ketone (enone) intermediate of the structure below,

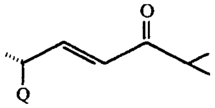

where Q is the vitamin D nucleus defined above.

After side chain attachment, the next essential step of the process is the reduction of the ketone group in the side chain to obtain the desired 24-hydroxy compound. This reduction can be accomplished with available hydride reducing agents, e.g. $LiAlH_4$, $NaBH_4$ and similar reagents, well documented in the art. Advantageously, this reduction step is accomplished with asymmetric hydride reducing agents, i.e. reagents that will reduce the ketone group stereoselectively to either the (R)- or the (S)-24-alcohol. A number of suitable reagents are known (Brown et al. J. Org. Chem. 52, 5406 (1987)). In this manner it is possible to convert the α,β-unsaturated ketone intermediate shown above to either the 24(R)-hydroxy or the 24(S)-hydroxyvitamin D derivative, characterized, respectively, by the structures shown below,

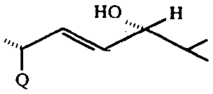 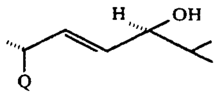

where Q represents the 1α-hydroxyvitamin D nucleus defined above. A final step, comprising the removal of hydroxy-protecting groups ($X^1$, $X^2$) then provides the desired vitamin D analogs, 1α,24(R)-dihydroxy-22(E)-dehydro-vitamin $D_3$ and 1α,24(S)-dihydroxy-22(E)-dehydrovitamin $D_3$.

It should be noted also that in the above process, the hydroxy-protecting groups may optionally be removed at an intermediary stage of the process. For example, the hydroxy-protecting groups $X^1$ and/or $X^2$ may be removed at the stage of the α,β-unsaturated ketone (enone) intermediates shown above, and the resulting free hydroxy compounds can then be subjected to the reduction step to obtain the desired 1α,24-dihydroxyvitamin D compounds.

For hydroxy protection, the groups $X^1$ and $X^2$ may be selected from the known hydroxy-protecting groups. Preferred are the alkylsilyl or alkylarysilyl groups (e.g., trimethylsilyl, triethylsilyl, t-butyldimethylsilyl, diphenylmethylsilyl, dimethylphenylsilyl) or alkoxyalkyl groups such as methoxymethyl, methoxyethoxymethyl, tetrahydropyranyl, or tetrahydrofuranyl.

SPECIFIC EMBODIMENT OF THE PROCESS

The process of this invention is further defined by the sequence of reactions illustrated in Process Scheme I and by the specific examples. In Process Scheme I, the starting material used is the hydroxy-protected 1α-hydroxyvitamin D-22-aldehyde as illustrated by structure 1 in the scheme. In structure 1, $X^1$ and $X^2$ represent hydroxy-protecting groups, e.g. any of the alkylsilyl, alkylarylsilyl or alkoxyalkyl groups previously defined. Side chain attachment is accomplished by the reaction of aldehyde 1 with an appropriate ylid reagent. Thus, treatment of 1 with isobutyrylmethylenetriphenylphosphorane, a known ylid reagent (U.S. Pat. No. 4,588,528), in an organic solvent provides the enone 2 in one step. The groups $X^3$ and $X^4$ in intermediates 2 may represent hydroxy-protecting groups as present in the starting material, compound 1. However, in 2, one or both of these hydroxy-protecting groups may also be removed under standard hydrolytic conditions to obtain the corresponding deprotected compounds, i.e. the intermediate 2 where $X^3$ and/or $X^4$ represent hydrogen. Both the hydroxy-protected or the free hydroxy forms of compound 2 are suitable for subsequent reactions of the process, it being understood, of course, that the choice of reagents and conditions in such subsequent reaction steps be compatible with the presence of either hydroxy-protecting groups or free alcohols, as is obvious to those skilled in the art.

In the next step of the process, the 24-ketone function of enone intermediate 2 is reduced with hydride reagents so as to obtain the corresponding 24-alcohol derivative. Advantageously this reduction is effected with one of the available chiral hydride reagents so as to generate selectively either the 24(R)- or the 24(S)-alcohol. A number of such stereoselective reducing agents are known (e.g. Brown et al. J. Org. Chem. 52, 5406–12, 1987). For example, by reduction of enone 2 with (R)-(+)-(2,2'-dihydroxy-1,1'-binaphthyl)-lithium aluminum hydride, there is obtained the 24(R)-alcohol product of structure 3 in Scheme 1. Analogously, the reduction of enone 2 with (S)-(−)-(2,2'-dihydroxy-1,1-binaphthyl)-lithium aluminum hydride provides the 24(S)-alcohol depicted as structure 4 in Scheme 1.

In a final step, hydroxy-protecting groups ($X^3$, $X^4$), if present, are removed under standard and known hydrolytic conditions to obtain the desired free hydroxy compounds, namely 1α,24(R)-dihydroxy-22(E)-dehydrovitamin $D_3$ (structure 3, where $X^3=X^4=H$) and 1α,24(S)-dihydroxy-22(E)-dehydrovitamin $D_3$ (structure 4, where $X^3=X^4=H$).

The invention is further described by the following specific examples of individual reactions and products. In these examples, compound specification is by Arabic numerals, e.g. compound 1, 2, 3, 4, etc. refer to the structures so numbered in Process Schematic 1. The abbreviation "TBDMS", as used in the Examples, signifies a t-butyldimethylsilyl hydroxy-protecting group.

EXAMPLE 1

1α-Hydroxy-22(E)-dehydro-24-oxo-vitamin $D_3$ 1,3-t-butyldimethylsilyl ether (2, $X^3=X^4=$TBDMS): To a solution of 100 mg (0.175 mmole) of the 22-aldehyde (1, $X^1=X^2=$TBDMS) in 3.0 ml in anhy. DMSO was added 345 mg (1.0 mmole) of isobutyrylmethylenetriphenylphosphorane and the reaction was stirred at 85° for 48 hrs under argon. At the end of this time, the reaction was diluted with 80 ml of hexane and washed with 2×60 ml of 3% HCl, 60 ml of sat. $NaHCO_3$, 60 ml of sat. NaCl dried over $Na_2SO_4$ and concentrated under vacuum to yield 117 mg of (2) as oil which crystallized upon standing. UV (max): 265, 225 nm. NMR ($CDCl_3$) δ, ppm: 0.15 (s, 12H, silyl Me), 0.57 (s, 3H), 0.87 (s, 18H, silyt t-butyl), 1.10 (d, J=9.5 Hz, 9H), 1.99 (m, 2H), 2.22 (dd, J=13.1, 7.36 Hz, 1H), 2.27 (m, 1H), 2.44 (dd, J=13.1, 2.6 Hz, 1H), 2.83 (m, 2H), 4.18 (m, 1H), 4.37 (m, 1H), 4.85 (s, 1H), 5.17 (s, 1H), 6.01 (d, J=11.3 Hz, 1H), 6.08 (d, J=15.4 Hz, 1H), 6.23 (d, J=11.3 Hz, 1H), 6.72 (dd, J=15.9, 8.9 Hz, 1H), mass spectrum, m/z 640 (M+), 508 (M+-HOTBDMS), 248; HRMS, calc. for $C_{39}H_{68}Si_2O_3$, 640.4707; found, 640.4706.

EXAMPLE 2

1α,24(R)-dihydroxy-22(E)-dehydrovitamin $D_3$ (3, $X^3=X^4=$TBDMS): To 550 μl of 1M $LiAlH_4$/THF was added 500 μl of anhy. THF and the stirred solution was cooled to 0° under argon. To this solution was added 520 μl of 1M EtOH/THF followed by 151 mg (0.53 mmole) of (R)-(+)-1,1'-bi-2-napthol and stirring was continued at 0° for 1 hr. At the end of this time, the reaction was cooled in a dry ice/acetone bath and 54 mg (0.085 mmole) of the 24-keto analog (2) from the previous reaction in 500 μl of THF was added dropwise. After 2 hr at −78° the reaction was brought to room temperature and quenched with wet ether. The crude reaction mixture was filtered through celite, concentrated to dryness under vacuum and flash chromatographed on 25 g of silica (5% EtOAc/Hex) to yield 39 mg of 24(R)-hydroxy derivative (3, $X^3=X^4=$TBDMS): UV (max): 265 nm. TLC: (8:2, Hex:EtOAc) $R_f$=0.52. 24(S)-isomer $R_f$=0.45.

EXAMPLE 3

1α,24(R)-dihydroxy-22(E)-dehydrovitamin $D_3$ (3, $X^3=X^4=H$): To a solution of 39 mg of the silyl-protected vitamin (as obtained in Example 2) in 1.0 ml of THF was added 0.5 ml of 1M TBAF/THF and the reaction was warmed to 50° for 2.5 hr. At the end of this time, the reaction was diluted with 40 ml of ether, washed with 2×25 ml of sat. NaCl, dried over $Na_2SO_4$, and concentrated under vacuum to yield 25.6 mg of crystalline product. The crude material was recrystallized from 750 μl of ethyl formate to yield 12.5 mg of the desired product, compound 3 ($X^3=X^4=H$), mp 150°–150.5°. TLC (15:85 $CH_3OH$:$CH_2Cl_2$) $R_f$=0.65. HPLC (Hypersil 3 μm, 0.46×15 cm; 11% 2-propanol/-hexanes; 1.5 ml/min) $t_r$=4.8 min. UV (ε): 265 nm (18,000); max/min: 169.

Process Scheme 1
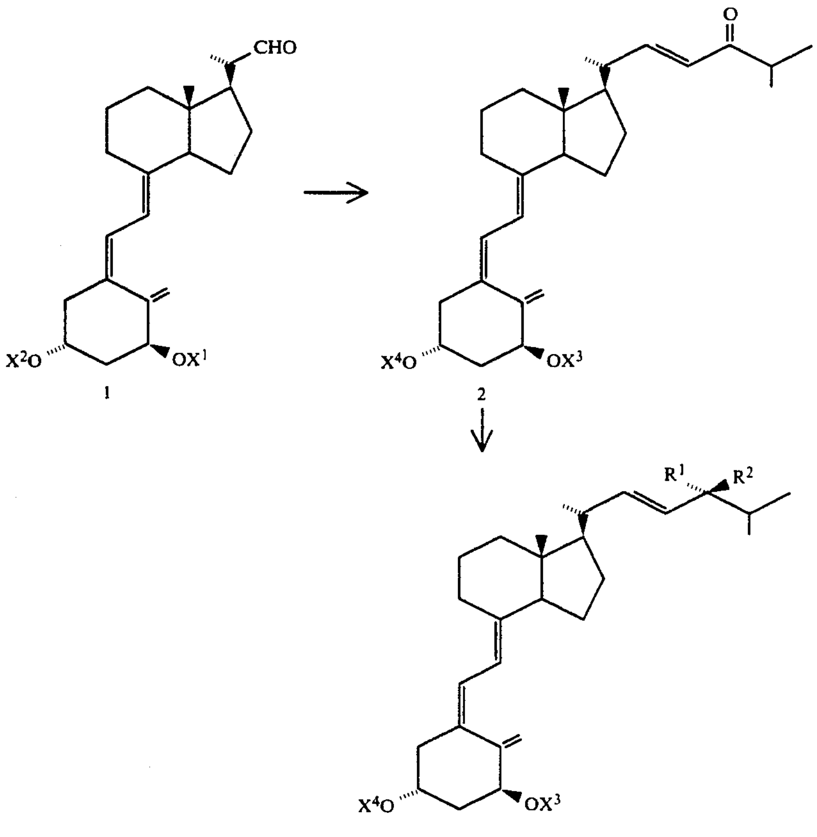
1
2
3: $R^1$ = OH, $R^2$ = H
4: $R^1$ = H, $R^2$ = OH
We claim:
1. Compounds of the formula,
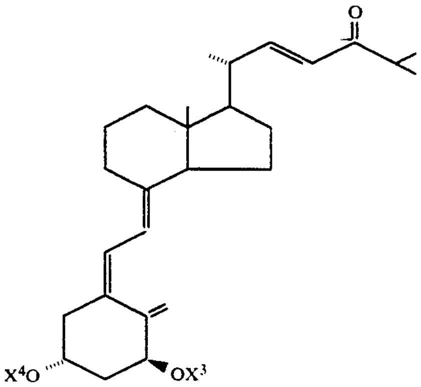
where $X^3$ and $X^4$, which may be the same or different, represent hydrogen or a hydroxy-protecting group.
* * * * *

UNITED STATES PATENT AND TRADEMARK OFFICE

CERTIFICATE OF CORRECTION

PATENT NO. : 5,247,104

DATED : September 21, 1993

INVENTOR(S) : Hector F. DeLuca et al

It is certified that error appears in the above-identified patent and that said Letters Patent is hereby corrected as shown below:

Column 1, between lines 3 and 5

--- This invention was made with United States Government support awarded by the National Institutes of Health (NIH), Grant No. DK-14881. The United States Government has certain rights to this invention.---

Signed and Sealed this

Thirty-first Day of May, 1994

Attest:

BRUCE LEHMAN

*Attesting Officer* *Commissioner of Patents and Trademarks*